US008551062B2

(12) United States Patent
Kay

(10) Patent No.: US 8,551,062 B2
(45) Date of Patent: Oct. 8, 2013

(54) MALE EXTERNAL INCONTINENCE DEVICE

(75) Inventor: Dennis M. Kay, Largo, FL (US)

(73) Assignee: BioDerm, Inc., Largo, FL (US)

( * ) Notice: Subject to any disclaimer, the term of this patent is extended or adjusted under 35 U.S.C. 154(b) by 0 days.

(21) Appl. No.: 12/874,986

(22) Filed: Sep. 2, 2010

(65) Prior Publication Data
US 2011/0230851 A1 Sep. 22, 2011

Related U.S. Application Data

(60) Provisional application No. 61/239,183, filed on Sep. 2, 2009.

(51) Int. Cl.
| | |
|---|---|
| *A61F 5/44* | (2006.01) |
| *A61F 5/451* | (2006.01) |
| *A61F 5/48* | (2006.01) |
| *A61M 25/00* | (2006.01) |
| *A61M 39/00* | (2006.01) |

(52) U.S. Cl.
USPC ........... 604/352; 604/180; 604/257; 604/264; 604/258; 604/544; 604/327; 604/346; 604/347; 604/355

(58) Field of Classification Search
USPC ................. 604/180, 257, 264, 285, 544, 327, 604/346, 347, 355, 352
See application file for complete search history.

(56) References Cited

U.S. PATENT DOCUMENTS

| | | | | | |
|---|---|---|---|---|---|
| 3,788,324 | A | * | 1/1974 | Lim | 604/352 |
| 4,419,097 | A | * | 12/1983 | Rowland | 604/174 |
| 4,626,250 | A | * | 12/1986 | Schneider | 604/352 |
| 5,078,707 | A | * | 1/1992 | Peter Klug | 604/349 |
| 5,087,252 | A | * | 2/1992 | Denard | 604/346 |
| 5,263,947 | A | | 11/1993 | Kay | |
| 5,643,235 | A | * | 7/1997 | Figuerido | 604/352 |
| 5,827,247 | A | | 10/1998 | Kay | |
| 5,830,932 | A | | 11/1998 | Kay | |
| 5,935,091 | A | * | 8/1999 | Friedman | 602/79 |
| 2001/0005782 | A1 | * | 6/2001 | Tanghoj et al. | 604/327 |
| 2002/0026163 | A1 | * | 2/2002 | Grundke | 604/347 |
| 2006/0122568 | A1 | * | 6/2006 | Elson et al. | 604/352 |
| 2007/0117880 | A1 | * | 5/2007 | Elson et al. | 523/118 |
| 2008/0183157 | A1 | * | 7/2008 | Walters | 604/544 |

* cited by examiner

*Primary Examiner* — Adam Marcetich

(57) ABSTRACT

A male external incontinence device includes a first seal formed of adhesive leaves carried by a housing and a second seal attached to the housing to be at a fixed position relative to the first seal and having a length to extend around the first seal after the leaves are secured to a penis.

6 Claims, 6 Drawing Sheets

MALE EXTERNAL INCONTINENCE DEVICE

CROSS-REFERENCE TO RELATED PATENT APPLICATION

This application claims priority from prior U.S. provisional patent application Ser. No. 61/239,183 filed Sep. 2, 2009, the entire disclosure of which is incorporated herein by reference.

BACKGROUND OF THE INVENTION

1. Field of the Invention

The present invention relates to external incontinence devices and, more particularly, to external urinary incontinence devices configured for the human male anatomy.

2. Brief Discussion of the Related Art

Male urinary incontinence is a common medical problem that is managed in the prior art with absorbent diapers, indwelling urinary catheters and/or external, non-invasive urine collection devices. Diapers are associated with a high rate of skin breakdown and decubitis ulcer formation while indwelling urinary catheters are a leading cause of urinary tract infections. Accordingly, there has been a great demand for non-invasive external incontinence devices for collecting urine from males without exposing the body to constant urine contact.

To avoid leakage, prior art external, non-invasive devices for collecting urine from males, as exemplified by U.S. Pat. No. 5,263,947 to Kay, U.S. Pat. No. 5,827,247 to Kay and U.S. Pat. No. 5,830,932 to Kay, have incorporated a parameatal seal formed of a ring or annular arrangement of leaves or petals carried by a urine drainage housing and adapted to be adhesively secured to the end of the penis to produce a seal preventing leakage of urine. To enhance the seal, additional sealing layers have been proposed; however, such sealing layers are frequently applied incorrectly when the application requires that the individual applying the device independently establish an optimal accurate application of the additional sealing layer(s). Application of the additional sealing layer(s) is commonly inaccurate, with the additional sealing layer(s) being applied too proximal or too distal to other sealing layer(s) or with inadequate alignment to achieve an optimal bilaminar seal. Each additional sealing layer must be applied in a specific spatial orientation with respect to previously applied sealing layers, to optimize the leak free duration of each device application.

There is a need for a male external incontinence device (MEID) which can be applied with a consistent spatial orientation to allow leak-free use.

SUMMARY OF THE INVENTION

In a primary aspect, the present invention relates to a male external incontinence device having first and second seals, the first seal being attached to a housing at a distal end thereof and the second seal being attached to the housing to be at a fixed position relative to the first seal and having a length to extend around the first seal after the leaves of the first seal are secured to the penis.

The MEID of the present invention improves accurate application of sealing layers and optimizes the creation and maintenance of an occlusive seal across a range of male anatomical variations. The MEID utilizes an assembly of components with dimensions and mechanical characteristics working in combination to address the physiological aspects of male anatomy and user dexterity.

The MEID of the present invention in one embodiment is formed of a fully flexible parameatal barrier body providing an occlusive seal combined with a housing which connects to urinary drainage tubing or an accessory such as an adapter or urine collection bag and a second seal arrangement affixed to the housing in an optimal orientation (rotation and distance from the barrier body). In such a configuration, the user experience is improved over prior art in that the parameatal barrier body and the second seal arrangement are presented to the user in the ideal orientation. A peel away release film detachment system facilitates application of the MEID.

The MEID of the present invention includes a bilaminar seal which uses laminated sheets of adhesive and polymer films to form a primary seal secured directly to the glans penis, and a secondary, circumferential seal surrounding the primary seal and provided in a fixed position relative to the primary seal.

The MEID of the present invention is provided with two independent parameatal sealing layers, each having a parafrenular gap to preserve foreskin freedom of movement and optimize the seal in the infra-meatal ventral surface of the glans. A first circumferential seal is created by anchoring the seal during manufacture to the outer or non-adhesive surface of the first barrier disc sealing layer thereby improving accuracy of application and improving inframeatal ventral surface seal, providing optimal conformation for an optimal duration of leak-free device application. The second layer of sealing material forms to the surface formed by the combination of the first sealing layer and the individual glans topography to create an enhanced bilaminar independent seal for longer-lasting, more dependable, sealing thereby reducing the risk of urine leakage. Attachment of the second sealing layer in a horizontal plane, perpendicular to the long axis of the penile shaft at a point that provides for consistent longitudinal overlap of the second sealing layer over the proximal edge of the first sealing layer and with the second sealing layer attached by its horizontal midpoint to the ventral midpoint of the most ventral portion of the first sealing layer ensures an accurate center on center bilaminar assembly with each layer providing the capability of a custom, one size fits all independent seal while optimizing the sealing capabilities of the bilaminar assembly. The optimal bilaminar sealing assembly capability is further enhanced by deploying each half of the adhesive surface of the second sealing layer in a plane perpendicular to the longitudinal axis of the penile shaft, from the ventral center of the inframeatal glans surface circumferentially to the dorsal surface of the glans. Accurate, consistent deployment of each hall of the adhesive sealing surface of the second sealing layer is provided by a peel away release film having two plow-folded film components meeting along the ventral midline of the second sealing layer. Utilization of transparent release film facilitates accurate second sealing layer placement prior to exposure of the adhesive surface. The peel away film has large (extending to the full perimeter of the second sealing layer) peel grip tabs to facilitate grip and removal of release film tabs. These large peel grip film tabs allow more effective use of the device by Individuals with neuromuscular disorders including spinal cord injury, Parkinson's Disease, ALS, Multiple Sclerosis, etc. wherein decreased hand and finger dexterity is common.

Although various adhesives may be used, an exemplary adhesive is a hydrocolloid in a thickness of preferentially 0.010-0.025" and the film is 0.005" or less in thickness and preferably less than 0.002". The hydrocolloid and film laminates forming the bilaminar seals have a high elasticity corresponding to extension at break of at least 200% and preferably 300% to accommodate continuously changing (swelling and shrinking) variations in the size and shape of the glans penis.

The parameatal barrier body is cut into a shape designed to engage the glans penis through a plurality of leaves to provide a seal with minimum of wrinkles of seal gaps. One of the leaves conforms to the parafrenular area of the penis. Optionally the MEID can incorporate a gap in the leaf, called hence the "frenular gap" which promotes free movement of the frenulum and foreskin so that the foreskin is able to return to the full forward position without injury. The gap also preserves foreskin freedom of movement and optimizes the seal in the inframeatal ventral surface of the glans and penile shaft. The housing is constructed of soft (less than 30 Shore A) polymer and affixed to the centerline of the parameatal seal. The housing is able to flex and provide relief from leverage forces on downstream drainage tubing and thereby resist seal disruption and protect tissue. The second of the bi-laminar films, the independent circumferential seal, is affixed on the soft housing a distance of 0.100"-0.150" from the parameatal barrier body and preferably 0.125". The construction of the independent seal of elastic and preferably hydrocolloid adhesive and polymer film is similar to the parameatal barrier body. The circumferential second seal contains a second frenular gap with the same function as the gap in the parameatal barrier body serving as the primary seal. The bilaminar films are each provided with clear peel away release films. The release films have large, easy to grab tabs suitable for users with impaired fine motor movement. The two halves of the peel-away release films meet along the midline of the device.

Some of the advantages of the MEID of the present invention include accurate placement of sealing members, completely external positioning, skin friendly and hypoallergenic materials, discreet, low-profile design, all urine directed immediately away from body and effective for all male anatomies—large, small, retracted, circumcised and uncircumcised.

Other aspects and advantages of the present invention will become apparent from the following description of the preferred embodiments taken in conjunction with the accompanying drawings, wherein like parts in each of the several figures are identified by the same reference characters.

DETAILED DESCRIPTION OF THE INVENTION

Figure 1:
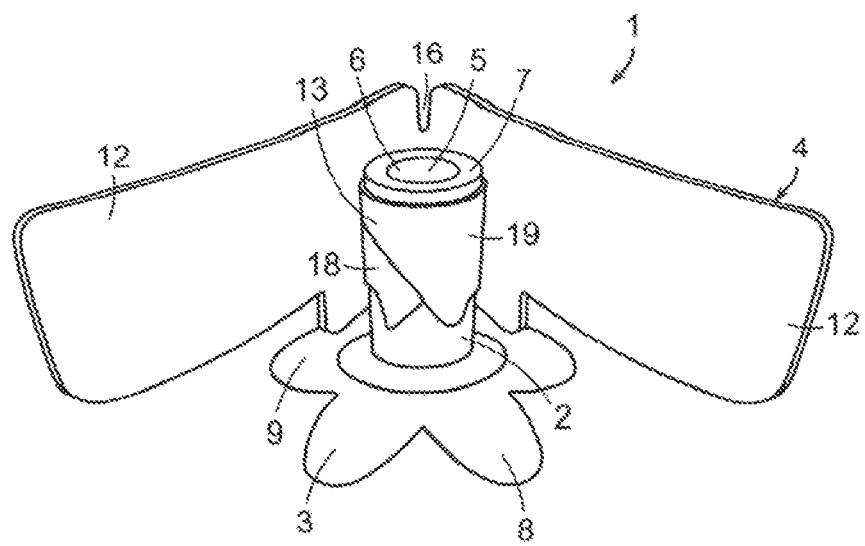
FIG. 1 is a perspective view of an MEM according to an exemplary embodiment of the present invention with a second seal member in a raised position.
Figure 2:
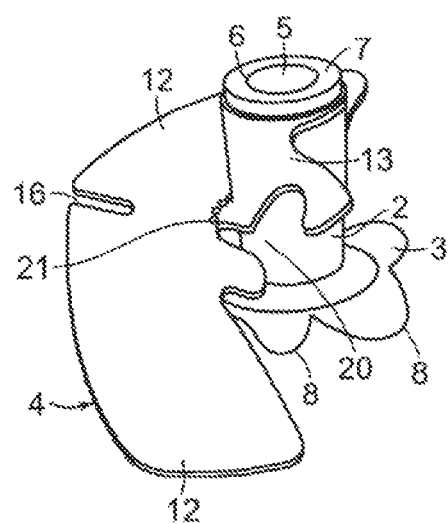
FIG. 2 is a perspective view of the MEID shown in FIG. 1, rotated approximately 90°, with the second seal member in an intermediate position.
Figure 3:
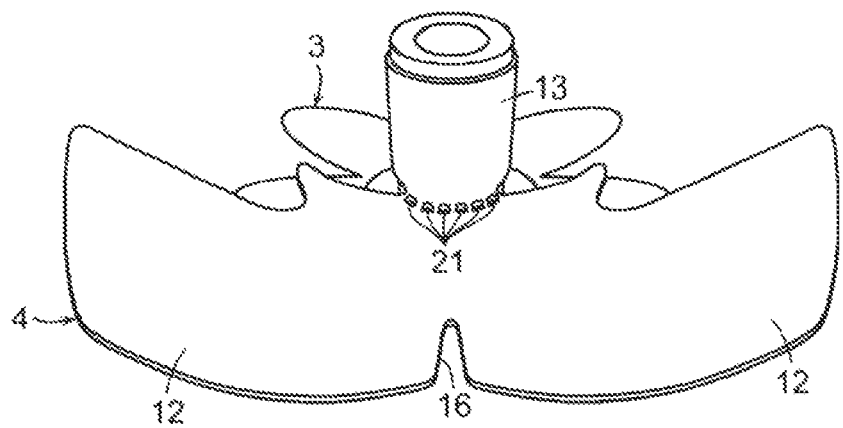
FIG. 3 is a perspective view, opposite that of FIG. 2.

As shown in FIGS. 1, 2, 3 and 4, a male external incontinence device (MEID) 1 according to an exemplary embodiment of the present invention includes a housing 2, a parameatal barrier body 3, and an independent (second) seal 4. Housing 2 has a lumen 5 therethrough with an upper (looking at FIGS. 1, 2 and 3), or proximal or outlet opening 6 at an annular surface. The parameatal barrier body 3 includes a plurality of leaves or petals 8 which are interconnected and arranged in a ring-like orientation forming an opening in the parameatal barrier body 3 allowing unimpeded urine flow into a distal inlet opening in housing 2 communicating with lumen 5. The parameatal barrier body 3 has an outer nonadhesive surface 9. The leaves 8 establish a primary or first seal with the parameatal surface of the glans penis. Upon removal of release films, the plurality of leaves are applied and smoothed onto the glans penis. The sealing application of each successive leaf of the plurality of leaves 8 can partially overlap the previously applied leaf seal. Each leaf of the plurality of leaves forms a substantially smooth seal that prevents wrinkles or ridges which otherwise could be capable of becoming a leak pathway for urine. The parameatal barrier body 3 is attached to the lower surface of housing 2 such that the distal inlet opening of housing 2 substantially coincides with the opening of the parameatal barrier body 3. The housing 2 is constructed of a soft, preferably less than 30 Shore A, polymer. The housing 2 is able to flex and provide relief from leverage forces on downstream drainage tubing and thereby resist seal disruption and protect tissue.

An independent second seal 4 further prevents urine leakage. The orientation and alignment of independent seal 4 relative to the parameatal barrier body 3 in the MEID is achieved by attaching seal 4 to the housing 2. Independent seal 4 includes opposingly extending wing-like seal members 12 and a central portion 13 which attaches independent seal 4 to the circumferential periphery of housing 2 such that portion 13 partially overlaps itself as shown at 18 and 19. Portion 13 adhesively attaches to housing 2 so that there is a consistent spatial orientation between independent seal 4 and parameatal barrier body 3. The consistent spatial orientation includes the spatial orientation gap between the independent seal 4 and parameatal barrier body 3 and the spatial orientation alignment of a parafrenular gap 16 between the seal members 12 to a longitudinal sagittal midline of the parafrenular leaves. Parafrenular gap 16 is located along a longitudinal sagittal midline 17 between seal members 12, to preserve foreskin freedom of movement and optimize the sealing of independent seal member 4 in the inframeatal ventral surface of the glans penis. The consistent spatial orientation establishes an optimally accurate application of independent seal member 4 enclosing the first parameatal seal on the glans penis in achieving an optimal bilaminar seal. Independent seal member 4 attaches in a substantially plane perpendicular to the long axis of the penile shaft at a point that provides for consistent longitudinal sealing over the edges of the parameatal barrier body 3. Independent seal member 4 attaches at its midpoint to the ventral midpoint of the most ventral portion of the attached parameatal barrier body 3 to the glans penis ensuring an accurate center-on-center, one size fits all bilaminar assembly. Independent seal 4 can have a plurality of perforations 21 between the seal members 12 and the portion 13. Accordingly, independent seal 4 can be detached from portion 13 by tearing along perforations 21 for placement where the established orientation and spacing is not effective due to physiological characteristics of a particular penis.

Independent seal 4 includes an adhesive surface which can be formed of a hydrocolloid. Each seal member 12 of seal 4 is adhesively attached to the glans penis over the leaves 8 from the ventral center of the inframeatal glans surface circumferentially to the dorsal surface of the glans penis. Both the parameatal barrier body 3 and independent seal 4 are composed of laminated sheets of adhesive films and polymer films. In an exemplary embodiment, the adhesive surface can be a hydrocolloid in a thickness of 0.010-0.025" and the film can be 0.005" or less in thickness and preferably less than 0.002". The hydrocolloid and film laminates forming the bilaminar seals have a high elasticity to accommodate continuously changing variations in the size and shape of the glans penis due to swelling and shrinking.

Figure 4:
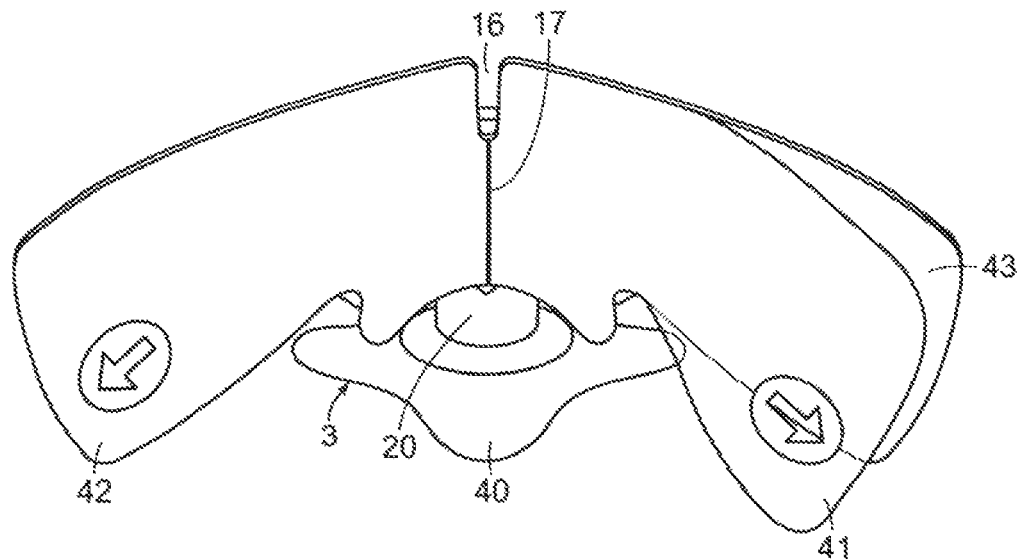
FIG. 4 is a perspective view, opposite that of FIG. 1.

FIG. 4 shows a pair of peel away release films 41 and 42 having plow-folded film components meeting along the longitudinal sagittal midline 17 of independent seal 4. The peel away release films 41 and 42 can be transparent to facilitate accurate placement prior to exposure of the adhesive surface. The peel away release films 41 and 42 have large, peel grip tabs, extending to the full perimeter of the second sealing layer to facilitate grip and removal of the release films. The spatial orientation gap 20 between the parameatal barrier body 3 and independent seal 4 can be seen in FIG. 4 where independent seal 4 is folded along perforations 21 to an upper position. In an exemplary embodiment, the independent seal 4 is affixed on the housing 2 a distance of 0.100"-0.150" from the parameatal barrier body 3 fanning the consistent spatial orientation gap 20, of 0.125," for example. A parafrenular leaf 40 is also shown in FIG. 4 where parafrenular leaf 40 forms a seal on the inframeatal ventral surface of the glans penis. Optionally, parafrenular leaf 40 may also have a parafrenular leaf gap (shown in FIG. 6) located along a longitudinal sagittal midline of the parafrenular leaf which preserves foreskin freedom of movement and optimizes the seal in the inframeatal ventral surface of the glans and penile shaft.

Figure 5:
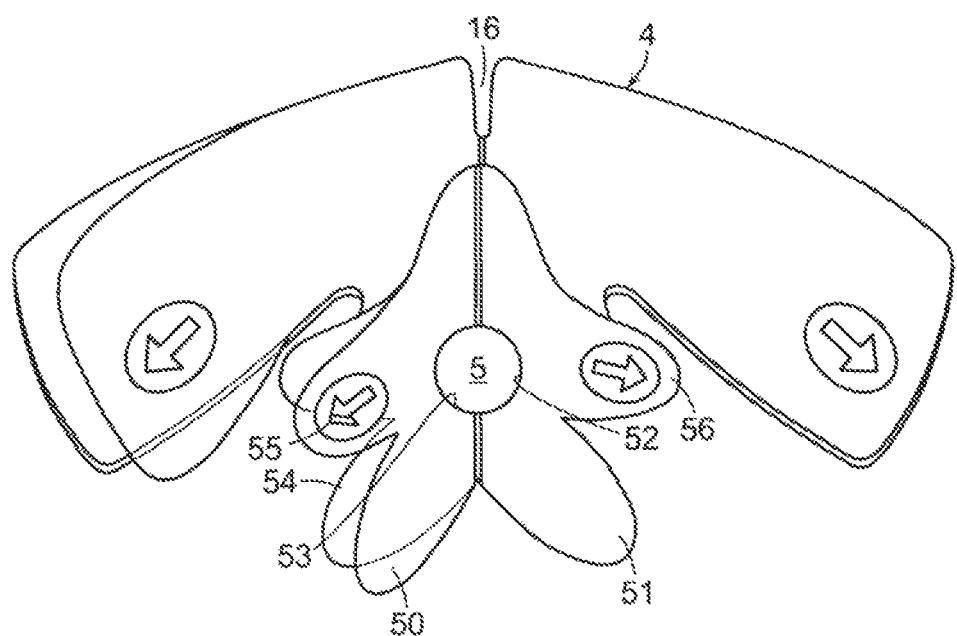
FIG. 5 is a bottom view of the MEID as shown in FIGS. 2 and 3.

FIG. 5 shows a bottom perspective view of the parameatal barrier body 3, independent seal 4, and an opening 52 to housing 2. The parameatal barrier body opening 53 is substantially similar to the lower opening 52 so as to not impede flow through the lumen 5 to the outlet tube of a urine collection channel. The lumen 5 of housing 2 extends from the outlet opening 6 at the surface 7 of housing 2 to the inlet opening 52 at the distal surface of housing 2. Parameatal barrier body 3 includes at least two leaves of varying size and shape, and preferably a number of leaves of varying size and shape to insure partial overlapping of the leaves forming a leak-proof seal. The parameatal barrier body 3 includes an upper nonadhesive surface 9 and a lower adhesive surface 54. The lower adhesive surface 54 of the parameatal barrier body 3 is covered by peel away release films 50 and 51. Peel away release films 50 and 51 are plow-folded and meet along the longitudinal sagittal midline of the parameatal barrier body 3 facilitating deployment of each half of the adhesive surface 54 of the parameatal barrier body 3. The pair of peel away release films 50 and 51 may be transparent to facilitate accurate parameatal barrier body positioning prior to exposure of the adhesive surface 54. The peel away release films 50 and 51 have large peel grip tabs 55 and 56, facilitating grip and removal of peel away release films 50 and 51. The easy grip and removal of release films 50 and 51 helps individuals with decreased hand finger dexterity suffering from neuromuscular disorders including spinal cord injury, Parkinson's disease, ALS, and Multiple Sclerosis.

Figure 6:
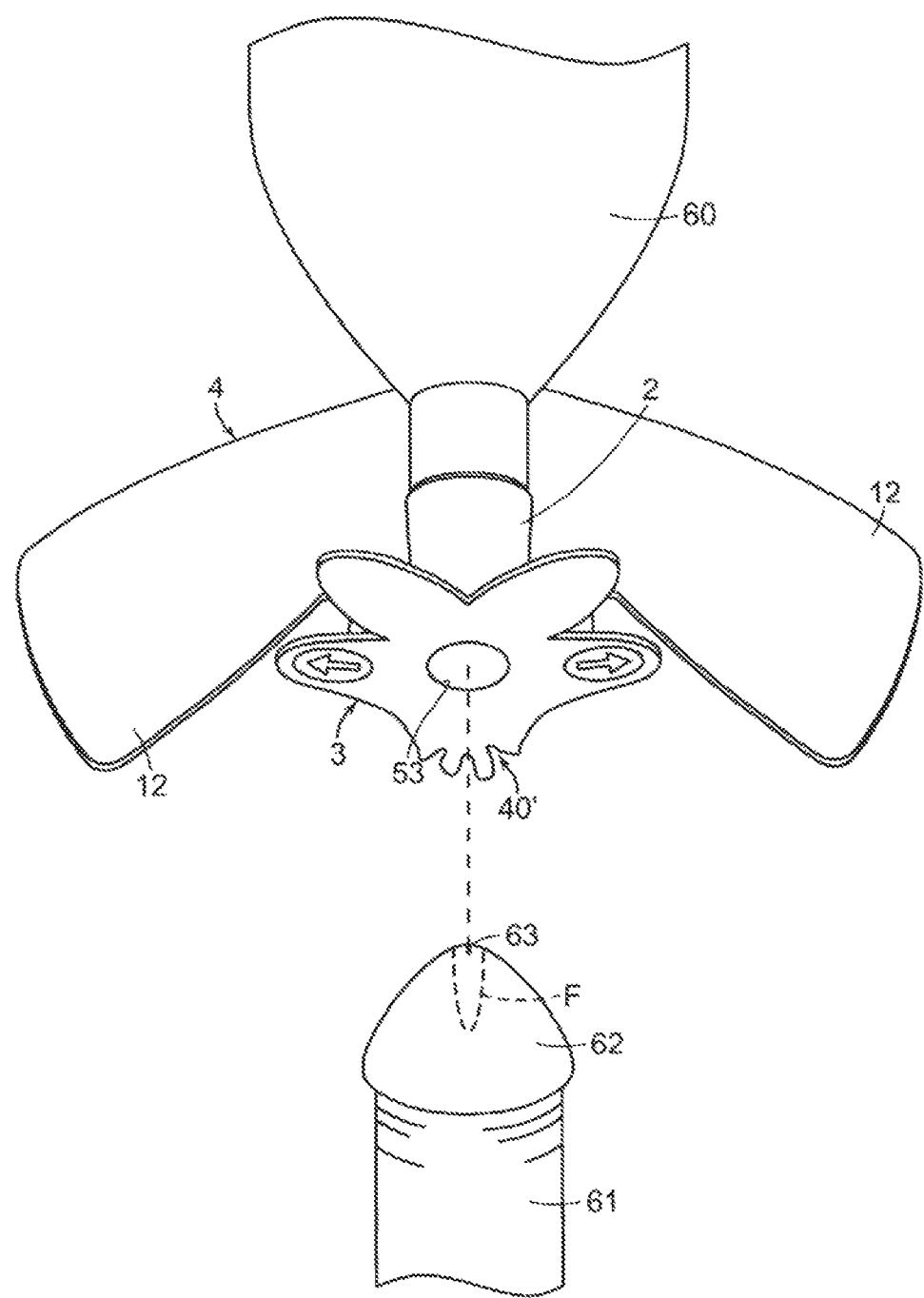
FIG. 6 is an exploded view of the MEID and a penis, illustrating alignment of the parameatal barrier body and meatal urethra.
Figure 7:
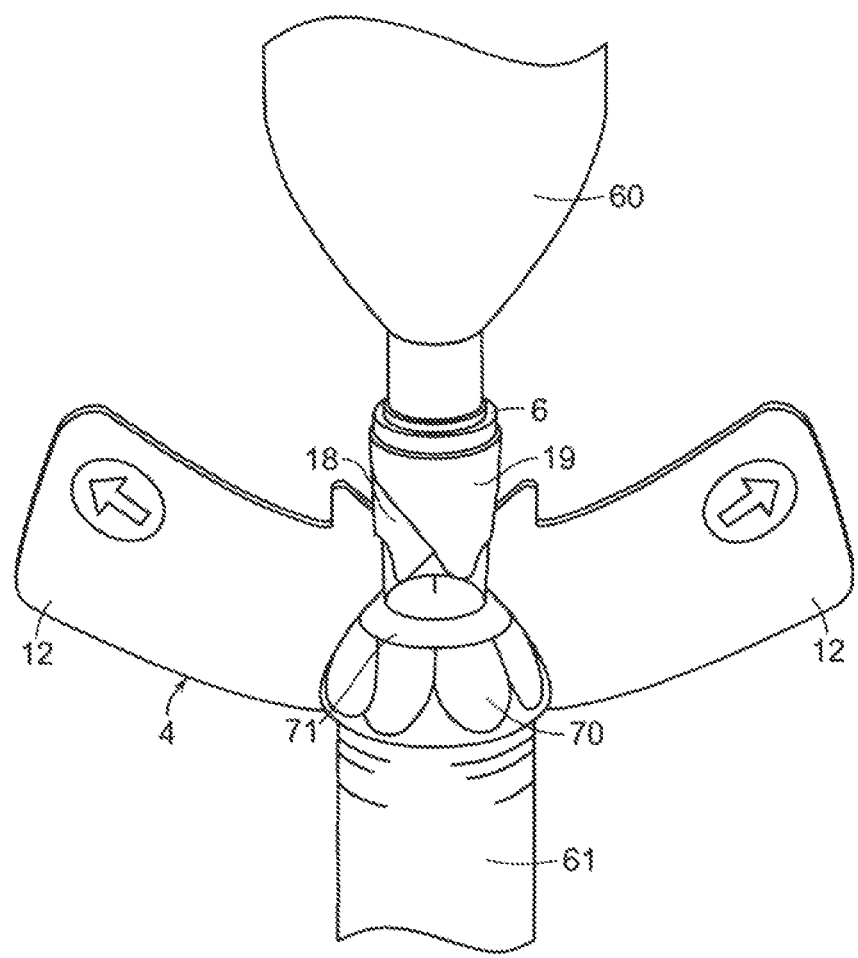
FIG. 7 is a perspective view of the MEID and a penis, illustrating the parameatal barrier body of the MEID forming a first parameatal seal with the glans penis prior to deployment of the second seal member.
Figure 8:
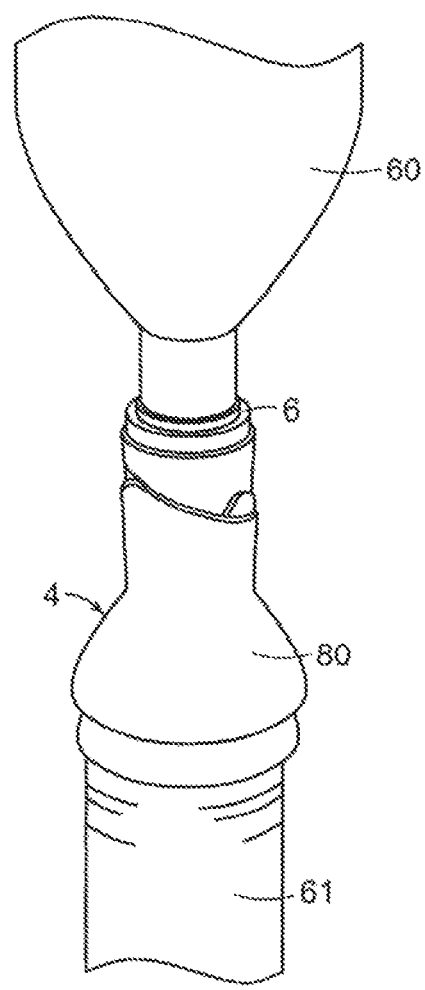
FIG. 8 is a perspective view of the MEID and a penis subsequent to deployment of the second seal member.

FIGS. 6-8 show a method of applying the MEID. As shown in FIG. 6, housing 2 communicates with a urine collection bag 60. The parameatal barrier body opening 53 of parameatal barrier body 3 is aligned with the meatal urethra 63. Rotational orientation is achieved by aligning parafrenular leaf 40 or the center gap in alternative parafrenular leaf 40' to conform to the parafrenular area (F shown in dashed lines) of the penis 61. Once properly aligned, the parameatal barrier body 3 is placed on the tip of the penis 61 allowing free flow of urine from the meatal urethra to the urine collection bag through lumen 5. The peel away release films 50 and 51 are removed exposing the adhesive surfaces of the leaves. A first parameatal seal is formed after each leaf of the plurality of leaves is attached to the glans penis beginning with the application of the parafrenular leaf 40 or 40' to the underside of the glans penis. The plurality of leaves may partially overlap during application shown in FIG. 7 at 70. The plurality of leaves are smoothed onto the glans penis to prevent leakage.

As shown in FIG. 7, prior to application of independent seal 4, independent seal 4 is properly oriented so that the peel away release film faces the underside of the glans penis. Due to the consistent spatial orientation of the parameatal barrier body 3 and independent seal 4, frenular gap 16 of independent seal 4 is prealigned with the frenulum F as a result of aligning the parafrenular leaf 40 and frenular area. The pair of peel away release films 41 and 42 are removed prior to applying the seal members 12 of independent seal 4. Seal members 12 enclose the first parameatal barrier body seal, shown at 71, forming a second parameatal seal 80 as shown in FIG. 8. Independent seal members 12 may overlap during application, and the second seal at 80, may be pressed into any grooves or ridges in the skin to prevent leakage. Independent seal members 12 can be separated from portion 13 at perforations 21 where required due to size or configuration of the penis.

Inasmuch as the present invention is subject to many variations, modifications and changes in detail is intended that all subject matter discussed above or shown in the accompanying drawings be interpreted as illustrative only and not be taken in a limiting sense.

What is claimed is:

1. A male external incontinence device comprising
   a housing made of a soft polymer and having an outlet opening, an inlet opening and a lumen extending between said inlet and outlet openings permitting passage of urine therethrough;
   a first seal attached to said housing to be disposed adjacent said inlet opening and including a plural of adhesive leaves in a ring-like arrangement around an opening aligned with said inlet opening in said housing, said leaves being adapted to be adhesively secured to the glans penis without obstructing the urethral meatus; and
   a second seal attached to said housing to be at a fixed position relative to said first seal and to be independent of said first seal,
   said second seal defining opposed, wing-like adhesive seal members with a central portion therebetween,
   said second seal members extending in opposite directions from said central portion to be wrapped around said first seal and circumferentially around the glans penis in normally overlapping opposite directions, said second seal having a length to extend around said first seal after said leaves are secured to the glans penis, said second seal being attached to said housing at said central portion and said second seal having a parafrenular gap between said seal members aligned with said mid-line.

2. The male external incontinence device recited in claim 1 wherein said first and second seals are made of hydrocolloid.

3. The male external incontinence device recited in claim 2 wherein said central portion of said second seal is wrapped around said housing to attach said second seal to said housing.

4. The male external incontinence device recited in claim 3 wherein said central portion is perforated.

5. The male external incontinence device recited in claim 4 further comprising plow-fold release films on said first and second seals.

6. The male external incontinence device recited in claim 1 herein said second seal has a length allowing said seal members to overlap.

\* \* \* \* \*